United States Patent
Brunelli et al.

(10) Patent No.: US 9,177,774 B2
(45) Date of Patent: Nov. 3, 2015

(54) CONTINUOUS FLOW MOBILITY CLASSIFIER INTERFACE WITH MASS SPECTROMETER

(75) Inventors: Nicholas Brunelli, Atlanta, GA (US); Konstantinos P. Giapis, Pasadena, CA (US); Richard C. Flagan, Pasadena, CA (US); Jesse L. Beauchamp, La Canada Flintridge, CA (US); Evan Neidholdt, Glendale, CA (US)

(73) Assignee: California Institute of Technology, Pasadena, CA (US)

( * ) Notice: Subject to any disclaimer, the term of this patent is extended or adjusted under 35 U.S.C. 154(b) by 114 days.

(21) Appl. No.: 13/008,697

(22) Filed: Jan. 18, 2011

(65) Prior Publication Data

US 2011/0174964 A1 Jul. 21, 2011

Related U.S. Application Data (60) Provisional application No. 61/295,643, filed on Jan. 15, 2010.

(51) Int. Cl.
| | |
|---|---|
| B01D 59/44 | (2006.01) |
| H01J 49/16 | (2006.01) |
| G01N 27/62 | (2006.01) |
| G01N 30/72 | (2006.01) |

(52) U.S. Cl.
CPC ............ *H01J 49/165* (2013.01); *G01N 27/624* (2013.01); *G01N 30/7233* (2013.01)

(58) Field of Classification Search
None
See application file for complete search history.

(56) References Cited

U.S. PATENT DOCUMENTS

| | | | | |
|---|---|---|---|---|
| 5,114,439 | A * | 5/1992 | Yost et al. | 95/18 |
| 5,117,190 | A | 5/1992 | Pourprix | |
| 5,596,136 | A * | 1/1997 | Flagan et al. | 73/28.04 |
| 5,606,112 | A * | 2/1997 | Flagan et al. | 73/28.04 |
| 5,847,386 | A * | 12/1998 | Thomson et al. | 250/288 |
| 5,869,831 | A | 2/1999 | De La Mora et al. | |
| 5,922,976 | A * | 7/1999 | Russell et al. | 73/865.5 |
| 6,259,101 | B1 * | 7/2001 | Wexler et al. | 250/423 P |
| 6,515,279 | B1 * | 2/2003 | Baykut | 250/285 |
| 6,567,157 | B1 * | 5/2003 | Flagan et al. | 356/37 |
| 6,621,077 | B1 * | 9/2003 | Guevremont et al. | 250/292 |
| 6,949,740 | B1 * | 9/2005 | Sheehan et al. | 250/288 |
| 7,626,161 | B2 * | 12/2009 | Labowsky et al. | 250/283 |
| 7,728,253 | B2 * | 6/2010 | Hopwood | 219/121.46 |
| 7,838,826 | B1 * | 11/2010 | Park | 250/288 |
| 7,928,374 | B2 * | 4/2011 | Rus-Perez et al. | 250/292 |
| 8,232,519 | B2 * | 7/2012 | De La Mora et al. | 250/281 |
| 2002/0053636 | A1 * | 5/2002 | Shiokawa et al. | 250/281 |
| 2002/0125423 | A1 * | 9/2002 | Ebeling et al. | 250/288 |
| 2007/0272847 | A1 * | 11/2007 | Labowsky et al. | 250/283 |

(Continued)

OTHER PUBLICATIONS

Zhang et al. ("Radial Differential Mobility Analyzer", Aerosol Science and Technology 23:357-372 (1995)).*

(Continued)

*Primary Examiner* — Andrew Smyth
(74) *Attorney, Agent, or Firm* — Gates & Cooper LLP (57) ABSTRACT

A continuous flow mobility classifier provide the ability to perform two-dimensional separation in mass spectrometry. An ionization system is used to ionize a sample. A differential mobility analyzer (DMA) (e.g., a nano-radial DMA) is coupled to the ionization system and to a mass spectrometer. The nano-RDMA is configured to separate the ionized sample by mobility for subsequent mass analysis by the mass spectrometer.

14 Claims, 9 Drawing Sheets

(56) References Cited

U.S. PATENT DOCUMENTS

| | | | |
|---|---|---|---|
| 2007/0273384 A1* | 11/2007 | Sheverev | 324/464 |
| 2008/0185513 A1* | 8/2008 | Belov et al. | 250/288 |
| 2008/0251714 A1* | 10/2008 | Juan et al. | 250/288 |
| 2008/0305479 A1* | 12/2008 | Van Den Boom | 435/6 |
| 2009/0134322 A1* | 5/2009 | Thomson | 250/282 |
| 2009/0321655 A1* | 12/2009 | Makarov et al. | 250/396 R |
| 2010/0072391 A1* | 3/2010 | Hopwood | 250/397 |
| 2010/0213366 A1* | 8/2010 | Fernandez De La Mora et al. | 250/282 |
| 2011/0174966 A1* | 7/2011 | Wollnik et al. | 250/286 |

OTHER PUBLICATIONS

Zhang et al., ("Radial Differential Mobility Analyzer". Aerosol Science and Technology, vol. 23, (1995), pp. 357-372).*

International Search Report mailed Oct. 7, 2011, International application No. PCT/US2011/021553, International filing date Jan. 18, 2011.

Flagan, "Differential Mobility Analysis of Aerosols: A Tutorial". KONA Powder and Particle Journal, vol. 26, (2008), pp. 254-268.

Zhang et al., "Radial Differential Mobility Analyzer". Aerosol Science and Technology, vol. 23, (1995), pp. 357-372.

Brunelli, N. et al., "Radial differential mobility analyzer for one nanometer particle classification," Aerosol Science and Technology, 43:53-59, 2009.

Flagan, R., "On differential mobility analyzer resolution," Aerosol Science and Technology 30:556-570 (1999).

Guevremont, R. et al., "Combined ion mobility/time-of-flight mass spectrometry study of electrospray-generated ions," Anal. Chem. 1997, 69, 3959-3965.

Jiang, J. et al., "Transfer functions and penetrations of five differential mobility analyzers for sub-2 nm particle classification," Aerosol Science and Technology, 45:480-492, 2011.

De Juan, L. et al., "High resolution size analysis of nanoparticles and ions: running a vienna DMA of near optimal length at Reynolds numbers up to 5000," J. Aerosol Sci., vol. 29, No. 5/6, pp. 617-626, 1998.

Ruotolo, B. et al., "Ion mobility-mass spectrometry applied to cyclic peptide analysis: Conformational preferences of Gramicidin S and linear analogs in the gas phase," J. Am. Soc. Mass Spectrom., 2004, 15, 870-878.

Smith, J. et al., "Droplet evaporation and discharge dynamics in electrospray ionization," J. Phys. Chem. A 2002, 106, 9957-9967.

Ude, S. et al., "Molecular monodisperse mobility and mass standards from electrosprays of tetra-alkyl ammonium halides," Aerosol Science 36 (2005) 1224-1237.

De La Mora, J. F., "Diffusion Broadening in Converging Differential Mobility Analyzers", Journal of Aerosol Science 33, No. 3 (2002), pp. 411-437.

\* cited by examiner

CONTINUOUS FLOW MOBILITY CLASSIFIER INTERFACE WITH MASS SPECTROMETER

CROSS-REFERENCE TO RELATED APPLICATIONS

This application claims the benefit under 35 U.S.C. Section 119(e) of the following co-pending and commonly-assigned U.S. provisional patent application(s), which is/are incorporated by reference herein:

Provisional Application Ser. No. 61/295,643, filed on Jan. 15, 2010, by Nicholas Brunelli, Konstantinos P. Giapis, Richard C. Flagan, Jesse L. Beauchamp, and Evan Neidholdt, entitled "CONTINUOUS FLOW MOBILITY CLASSIFIER INTERFACE WITH MASS SPECTROMETER".

STATEMENT REGARDING FEDERALLY SPONSORED RESEARCH AND DEVELOPMENT

The invention was made with Government support under Grant Nos. CHE-0416381 and 0163981 awarded by the National Science Foundation. The Government has certain rights in this invention.

BACKGROUND OF THE INVENTION

1. Field of the Invention

The present invention relates generally to mass spectrometry, and in particular, to a method, apparatus, and article of manufacture for integrating a differential mobility analyzer with a mass spectrometer.

2. Description of the Related Art (Note: This application references a number of different publications as indicated throughout the specification by reference numbers enclosed in brackets, e.g., [x]. A list of these different publications ordered according to these reference numbers can be found below in the section entitled "References." Each of these publications is incorporated by reference herein.)

Two dimensional separation in mass spectrometry (MS) is an area under constant development. The analysis of mixtures often demands separation of the mixture before final analysis owing to the complexity of the mixture. Many techniques in mass spectrometry already exist and are well suited to mixture analysis. Liquid chromatography-mass spectrometry (LC-MS) is a widely used technique that has the greatest utility in pre-separating protein digests prior to mass spectrometry analysis. Ion mobility spectrometry mass spectrometry (IMS-MS) is an example of a two dimensional separation where the first dimension is the mobility of the ion and the second dimension is the mass of that ion.

The aforementioned preseparations operate in the time domain wherein a sample that is introduced at the entrance of the preseparation device are separated into fractions that arrive at the mass spectrometer entrance at times that vary according to specific physico-chemical properties of the analyte. A fast mass spectrometric analytical method such as time-of-flight mass spectrometry may be able to analyze the entire range of possible mass-to-charge-ratios on a time that is short compared to the time resolution of the preseparation method, but slower mass spectrometric methods may only be able to resolve a limited range of mass to charge ratios. If, however, the preseparation is capable of continuously transmitting a selected fraction of the sample, slower mass spectrometric methods may be able to resolve all of the components of the fraction. One example of such a continuous preseparation is field assymetric waveform ion mobility spectrometry (FAIMS™) which transmits molecules with mobilities within a narrow range of values to the mass spectrometer for sufficient time to resolve the analytes of interest within selected ion mobility fractions of the original sample.

While research implementations of mobility-MS experiments have been in existence for some time, commercial instrumentation for achieving mass-mobility measurements is nonetheless part of the state of the art in mass spectrometry instrumentation. Instrument companies have invested considerable dollars in the development of the latest class of instruments with mobility front ends. Advances in electronics and fabrication methods have finally enabled the mass production of such instruments on a scale commensurate with implementation in commercial laboratories. Examples of such instruments include Waters™ SYNAPT™ instruments and Thermo Scientific™ instruments using a field asymmetric waveform ion mobility spectrometry (FAIMS™) interface, as well as a number of instruments from smaller manufacturers. The fact that such research and development funding has been committed to the development of mobility-mass measurement is indicative that such instruments are desired and must continually be developed.

Accordingly, what is needed is a hybrid mass mobility instrument with a front-end mobility separation device. To better understand the problems of the prior art, a description of prior art mass spectrometry techniques is useful.

Mass spectrometry is an analytical technique used to identify unknown compounds, the isotopic composition of elements in a molecule and to determine the structure of a compound. Such identification is performed by measuring the mass-to-charge ratio of charged particles which can be used to determine the particle's mass, the composition of a sample, and/or the chemical structure of the sample/molecule.

In an MS process, a sample is loaded onto an instrument where it is vaporized (i.e., transitioned into a gas from a solid or liquid). The result is then ionized by a variety of methods to form charged particles (ions). The ions are separated by their mass-to-charge ratio in an analyzer, detected, and the ion signal is processed into mass spectra.

An MS instrument used to perform the above process may include an ion source, a mass analyzer, and a detector. The ion source is used to perform the vaporization and the ionization of the material under analysis (the analyte). Electrospray ionization (EI), where liquid containing the analyte is dispersed by electrospray into a fine aerosol, may be used during the ionization process. The ions are transported to the mass analyzer that sorts the ions by their masses (e.g., by applying electromagnetic fields). The detector measures the quantity of ions.

As described above, chromatographic techniques may be combined with MS to separate different compounds before analysis by the MS. LC-MS separates a liquid analyte (e.g., in combination with ES) before introducing the compound to the ion source and MS. IMS-MS first separates ions by drift time through a neutral gas under an applied electrical potential gradient before being introduced into an MS.

Embodiments of the present invention provide the ability to perform mobility separation before mass analysis by an MS. As set forth in the detailed description below, various different types of differential mobility analyzers (DMAs) may be used. For example, radial DMAs (RDMAs) may be used in one or more embodiments of the invention. Previously, a nano-RDMA device was presented and mobility values for various tetraalkylammonium ions were reported [1][7][8]. The previous experiment used an electrometer detection scheme where all ion current exiting the device was measured. However, prior art systems fail to integrate nano-RDMAs with an MS in an effective manner. Further, the prior art fails to integrate MS with DMAs that operate with flow rates that are compatible with general analytical laboratory operations.

SUMMARY OF THE INVENTION

A hybrid mass mobility instrument is described where an DMA instrument (e.g., a nano-RDMA instrument) is used as a front-end mobility separation device for electrospray ionization experiments. Specifically, organic salts or peptides have been shown to be analyzed by nano-RDMA, then analyzed in a second dimension in the quadrupole ion trap (QIT) mass spectrometer. Embodiments of the invention utilize a DMA system (e.g., a nano-RDMA-QIT system) developed by connecting the outlet of the DMA instrument to the atmospheric pressure inlet of an ion trap mass spectrometer. Incoming aerosols and ions from the electrospray source are separated by mobility in the DMA instrument, and are subsequently mass analyzed using the ion trap mass spectrometer.

This two dimensional approach has the advantage of a separation technique preceding mass analysis. For the nano-RDMA-MS experiment, embodiments of the invention demonstrate mobility analysis with mass spectrometric detection for tetraalkylammonium salts and the results compare well with previous experiments, confirming the peak assignments for the previous results. It can also be demonstrated that peptides may be analyzed with this instrument by analyzing Gramicidin S, a cyclic decapeptide. Embodiments of the invention may exhibit a resolution of approximately 5-7, and can increase the resolution by changing the ratio of aerosol and sheath gas flow rates.

BRIEF DESCRIPTION OF THE DRAWINGS

Referring now to the drawings in which like reference numbers represent corresponding parts throughout.

DETAILED DESCRIPTION OF THE PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview

Embodiments of the invention integrate/interface a DMA device (such as a nano-RDMA device) with an ion trap mass spectrometer so that MS detection can be achieved. The mobilities and corresponding mass spectra for several alkylammonium salts as well as for the cyclic decapeptide Gramicidin S were recorded. Also, the interfacing of the DMA device with the mass spectrometer provides a unique system from which hybrid mass-mobility measurements can be made. The interface is particularly simple and robust, with no major modification needed to either the mass spectrometer or the DMA instrument. The system may have particular utility in pre-separating charge states of peptides.

Detailed Description

Figure 1:
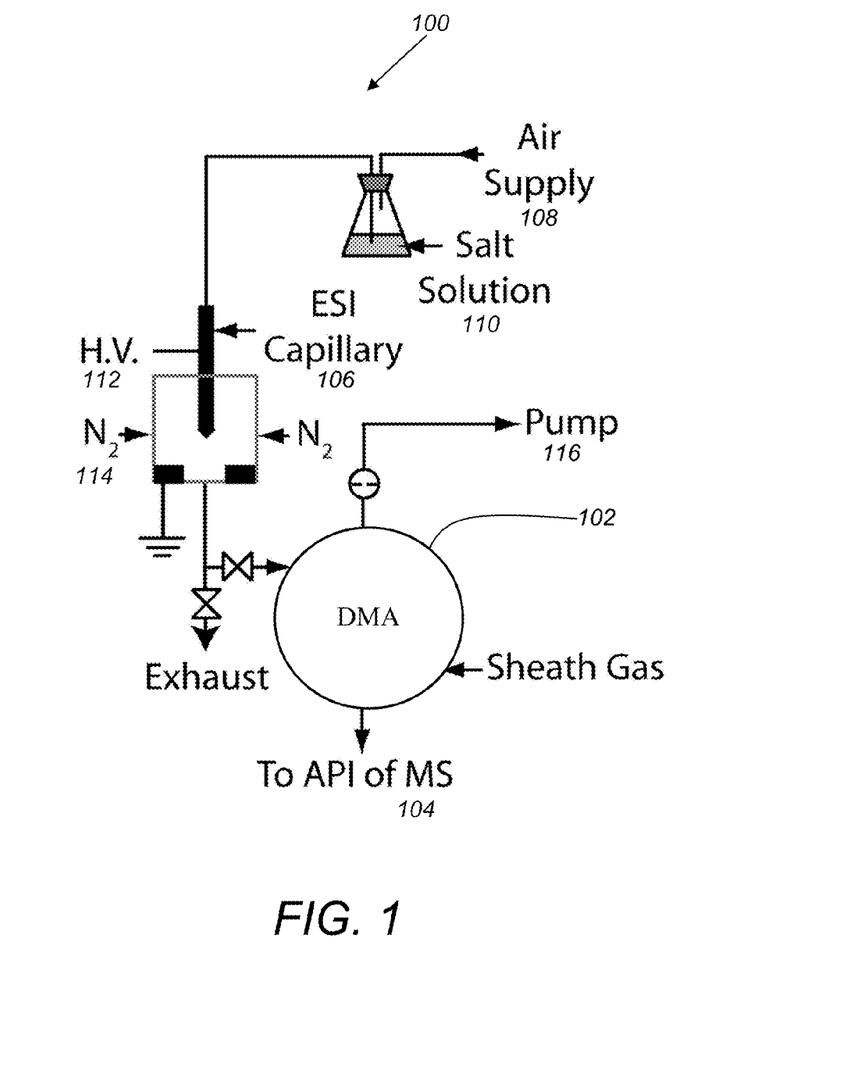
FIG. 1 illustrates a schematic of a DMA system interfaced to a mass spectrometer in accordance with one or more embodiments of the invention.

FIG. 1 illustrates a schematic of a DMA system interfaced to a mass spectrometer in accordance with one or more embodiments of the invention. More specifically, the schematic of FIG. 1 shows an experimental set up of a system 100 used to measure the combined mobility and mass distribution. DMA device 102 may be a DMA having a variety of shapes including radial (e.g., a nano-RDMA device).

The DMA instrument 102 is affixed to the entrance of a mass spectrometer 104 (i.e., to API of MS). The components of the system 100 are assembled in series in the following order: ionization source 106 (e.g., an eletrospray source), DMA 102, and mass spectrometer 104.

An exemplary MS 104 that may be used in embodiments of the invention is a Thermo Scientific™ LCQ Deca XP ion trap mass spectrometer (ITMS™). When using a standard mass spectrometer 104, modifications may not be necessary beyond the removal of the typical electrospray source and replacement with the DMA system 100 of embodiments of the invention. The ionization source 106 preceding the DMA 102 may be any type of electrospray ionization (ESI) emitter.

Air pressure (via air supply 108) is used to supply the analyte 110 (e.g., a salt solution) to the ESI capillary 106. The ESI capillary 106 ionizes the analyte 110 using high voltage 112 in a sheath gas 114 (e.g., nitrogen—$N_2$). The resulting ionized aerosol (that includes the ionized analyte and sheath gas) is transported to the DMA device 102 where it is pumped (using pump 116) to the MS.

Figure 2:
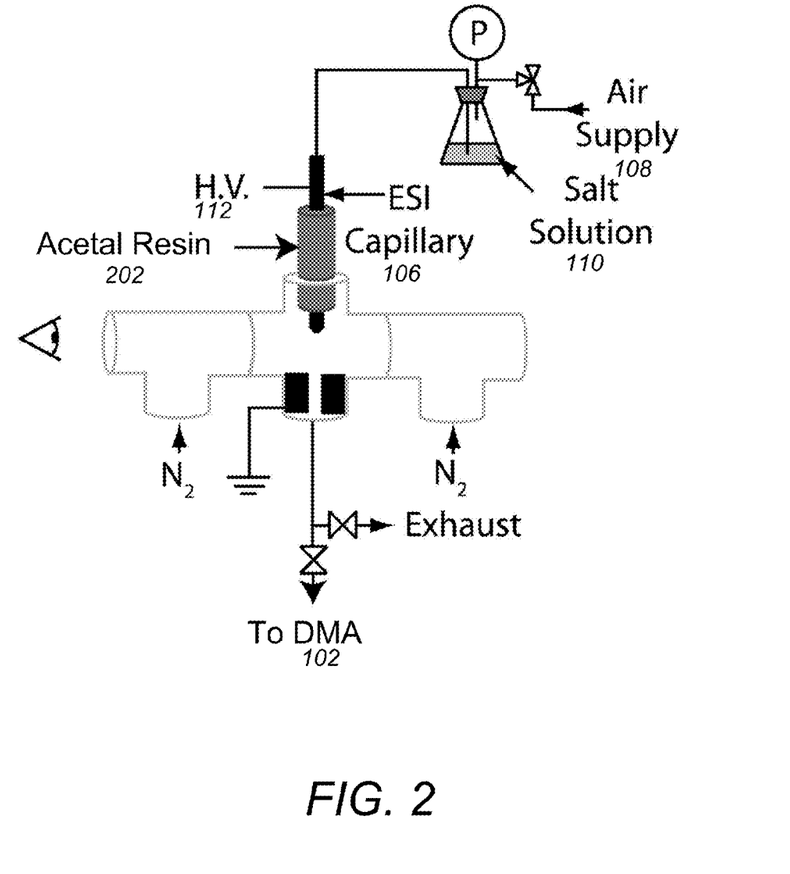
FIG. 2 illustrates a schematic of the ESI source 106 used in studies with alkylammonium cations in accordance with one or more embodiments of the invention.

FIG. 2 illustrates a schematic of the ESI source 106 used in studies with alkylammonium cations in accordance with one or more embodiments of the invention. The ESI source 106 has the feature of being able to observe the Taylor cone during electrospray using the viewing port. For the alkylammonium salts (e.g., salt solution 110), the electrospray source 106 may be the same used source as that used for calibration measurements. For Gramicidin S, the electrospray source 106 was of a miniaturized design based on the principles of that shown in FIG. 2. In FIG. 2, similar to that of FIG. 1, electrospray capillary 106 ionizes the analyte 110 via high voltage. To connect the ESI capillary 106 to the DMA 104 transportation mechanisms, the capillary 106 may be surrounded with an acetal resin 202 (e.g., acetal homopolymer) that maintains certain properties for the secure connection. The acetal resin 202 may be Delrin™ acetal resin manufactured by DuPont™.

Figure 3:
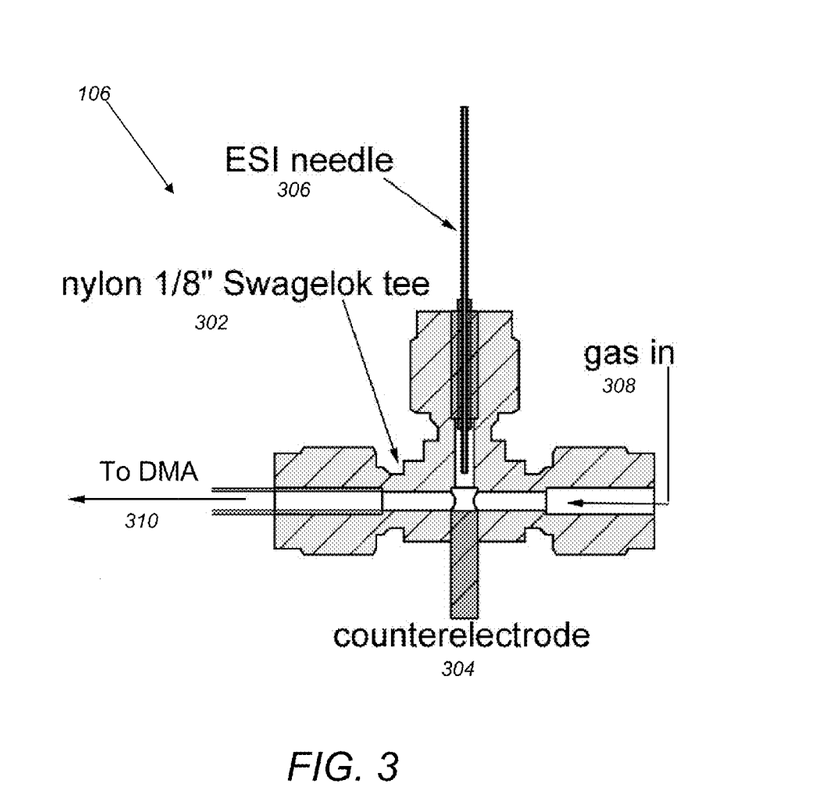
FIG. 3 shows an updated electrospray design in accordance with one or more embodiments of the invention.

FIG. 3 shows an updated electrospray design in accordance with one or more embodiments of the invention. The new electrospray source design affords operation at liquid flow rates more analogous to typical ESI experiments, much lower than the original ESI source design. For experiments with Gramicidin S, the ESI source may be operated at a voltage of +2400 V DC with a liquid flow rate of 5-10 µL/min. In FIG. 3, each electrospray source was connected to the DMA 102 using standard fittings (e.g., available from Swagelok™ corporation). The DMA 102 may be positioned in front of the LCQ-MS using a breadboard plate (150 mm×150 mm) made for mounting optical elements, a pair of custom-built mounting plates, and optic mounting posts (O.D.≈12 mm).

More specifically, FIG. 3 illustrates the detail of a miniaturized electrospray source 106 used in work with Gramicidin S. A ⅛" nylon Swagelok tee 302 was modified to accept a metallic counterelectrode 304. ESI needle 306 may be a 26 ga hypodermic tubing from Small Parts™ corporation. Application of high voltage 112 to needle 306 with grounded counterelectrode 304 establishes electric field for electrospray. Aerosol flow gas is introduced at "gas in" 308 and aerosol to be analyzed exits at "to DMA" 310. The miniaturized electrospray source allows for liquid flow rates that are similar to a typical electrospray ionization experiment (3-6 µL per min) which makes the exemplary embodiment of FIG. 3 compatible with typical commercial instrumentation for ESI using syringe pumps and limited sample volumes.

Figure 4:
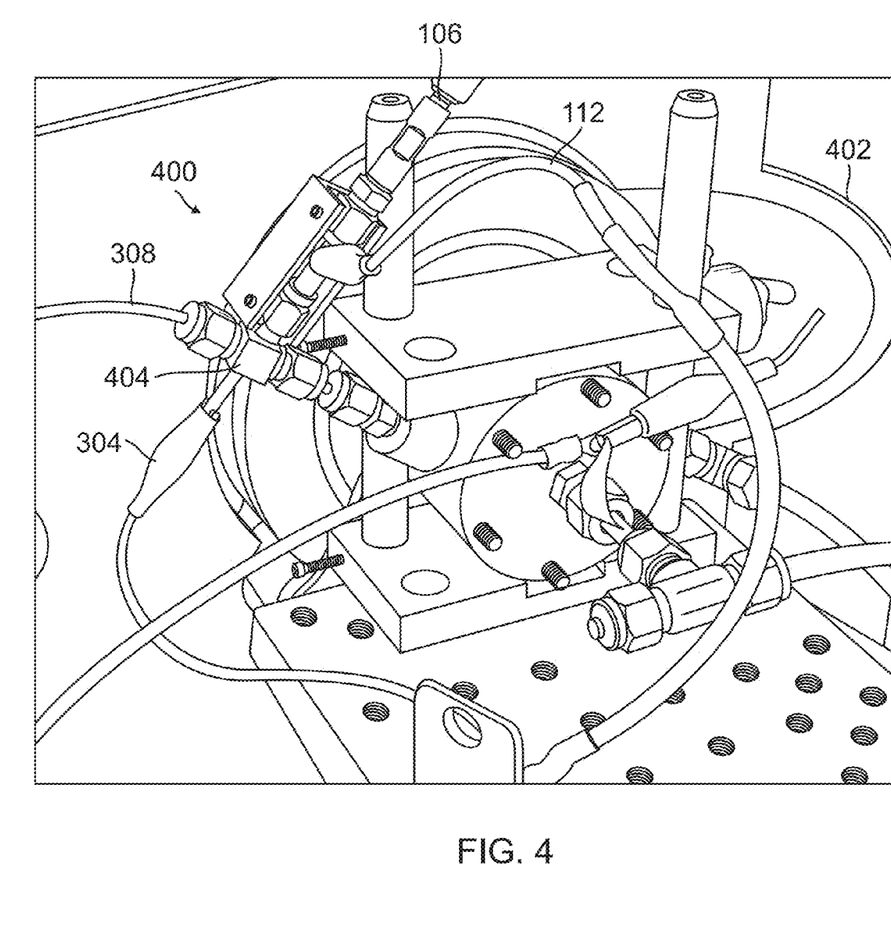
FIG. 4 is a photograph of an exemplary nano-RDMA instrument 400 installed in front of an ion trap mass spectrometer (ITMS) 402 in accordance with one or more embodiments of the invention.

FIG. 4 is a photograph of an exemplary nano-RDMA instrument 400 installed in front of an ion trap mass spectrometer (ITMS) 402 in accordance with one or more embodiments of the invention. Mounting is achieved using machined parts. The photograph also shows an electrospray source 106 made from nylon Swagelok™ fitting 404, as was used during Gramicidin S experiments. The illustrated assembly shows the sample outlet of the nano-RDMA 400 aligned with the atmospheric pressure inlet (API) of the ITMS 402. Due to the ports on the nano-RDMA 400 and the construction of the LCQ-MS, the sample outlet of the nano-RDMA 400 and the API of the LCQMS 402 were separated by a distance of 25 mm. The gap can be reduced to less than 1 mm by attaching a Swagelok (¼") to tube stub (⅛") fitting on the nano-RDMA outlet and empirically adjusting the position of the nano-RDMA 400 to minimize the gap between the instrument outlet and the atmospheric pressure inlet of the mass spectrometer 400. Further reductions in the separation distance may be achieved by redesign of the nano-RDMA outlet for optimal interfacing with the API of the mass spectrometer being used. Said modification may further involve modifications to the shape of the DMA to optimize the interface between the DMA and the mass spectrometer, e.g., using a DMA wherein charged particle classification is performed between conical electrodes that focus the classified ions at the apex of the conical section to facilitate efficient coupling of the DMA with the mass spectrometer inlet.

Figure 5:
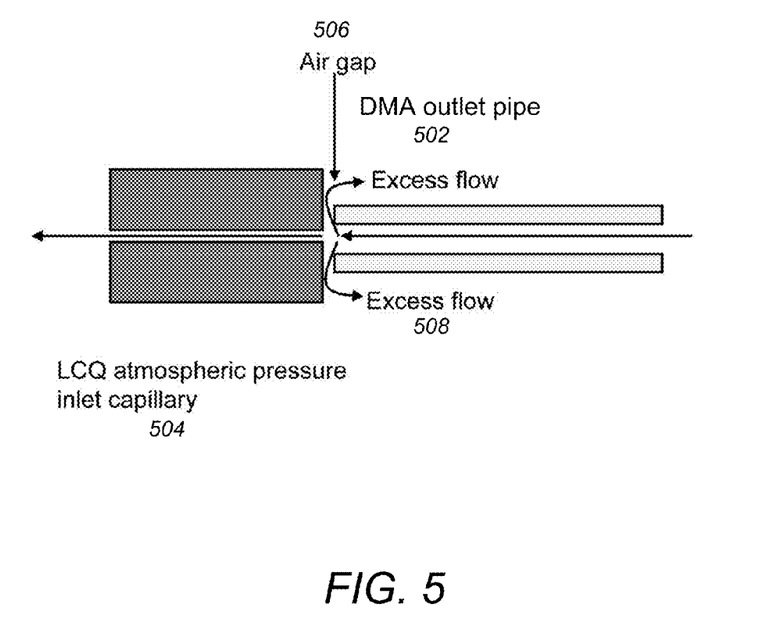
FIG. 5 illustrates a schematic of the interface between a DMA instrument and an MS in accordance with one or more embodiments of the invention.

FIG. 5 illustrates a schematic of the interface between a DMA instrument 100 and an MS 402 in accordance with one or more embodiments of the invention. More specifically, FIG. 5 is a drawing showing the particular arrangement of the nano-RDMA outlet with respect to the atmospheric pressure inlet of the mass spectrometer. The outlet pipe 502 is brought to near contact with the atmospheric pressure inlet capillary 504 of the ion trap instrument. An air gap 506 is maintained between the DMA 502 and LCQ 504. Any excess aerosol flow 508 is exhausted to the atmosphere. The DMA 502 (e.g., a nano-RDMA) may be operated with a 10 SLM (standard liter per minute) sheath flow rate of nitrogen and in voltage stepping mode. The voltage on the DMA may be provided from a high voltage power supply (e.g., Ultravolt™ 2 kV supply) that is controlled externally (e.g., with a LabVIEW™ (National Instruments, Austin, Tex., USA) program and hardware). The external control may set the voltage level for each step of the scan, which remains constant for a 30-second interval. The process can be repeated for a number of voltages to cover a range of particle mobilities. In an exemplary experiment, the external control program was started at the same time that a time-based scan in the MS software was started with a duration long enough to ensure data would be collected over the complete voltage scan. The data was analyzed using a program (e.g., Matlab™) that averaged the signal produced by the molecular ions over the 30 second interval that the voltage was held constant.

Solutions for electrospray can be prepared from tetrapropylammonium iodide, tetrabutylammonium iodide, tetrapentylammonium iodide, tetrahexylammonium iodide, tetraheptylammonium bromide, and tetraoctylammonium bromide salts which may be purchased from chemical suppliers. Each of the above indicated compounds may be present in solution at a concentration of 0.02 to 0.05 mg/mL in methanol. Solutions of Gramicidin S were prepared from a sample of Gramicidin S hydrochloride (e.g., obtained from Sigma Aldrich™ (St. Louis, Mo., USA)). The peptide was present in solution at a concentration of 0.2 mg/mL in methanol with 0.1% acetic acid added to aid in ionization in positive mode.

Results and Discussion

Mobility Distributions for Alkylammonium Salts

Figure 6:
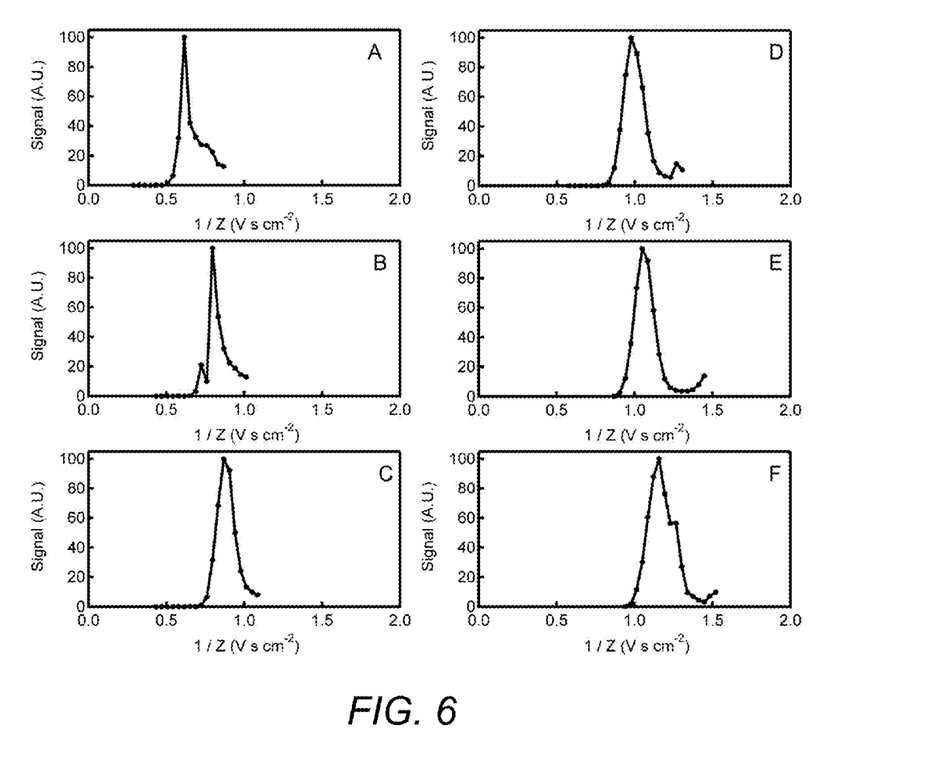
FIGS. 6A-6F illustrate inverse mobility distributions using a mass spectrometer as a detector in accordance with one or more embodiments of the invention.

The mobility distribution recorded using the LCQ-MS detector for the monomer of each alkylammonium ion (e.g., based on the configuration described above with respect to FIGS. 1-5) is presented in FIG. 6. More specifically, FIG. 6 illustrates distribution of observed signals as a function of inverse mobility (using a mass spectrometer as a detector). The inverse mobility distributions are recorded in respective figures with the ITMS as the detector for: FIG. 6A-tetrapropylammonium; FIG. 6B-tetrabutylammonium; FIG. 6C-tetrapentylammonium; FIG. 6D-tetrahexylammonium; FIG. 6E-tetraheptylammonium; and FIG. 6F-tetraoctylammonium cations. The molecular ion was detected at approximately the same voltage and 1/Z value reported previously when a Faraday cup electrometer was used as the detection, confirming the identity of the molecule detected. Table 1 compares the results obtained here to those previously obtained.

TABLE 1

| | 1/Z Value (V s cm−2) | | |
|---|---|---|---|
| Cation | de la Mora [5] | Brunelli [1] | This Work |
| tetramethylammonium | 0.459 | — | — |
| tetraethylammonium | | 0.531 | — |
| tetrapropylammonium | 0.619 | 0.619 | 0.62 |
| tetrabutylammonium | 0.718 | 0.721 | 0.79 |
| tetrapentylammonium | — | 0.837 | 0.88 |
| tetrahexylammonium | — | 0.937 | 0.98 |
| tetraheptylammonium | 1.030 | 1.032 | 1.05 |
| tetraoctylammonium | — | — | 1.16 |

As illustrated in Table 1, good agreement is observed indicating that detection using the mass spectrometer does not skew mobility values.

Figure 7:
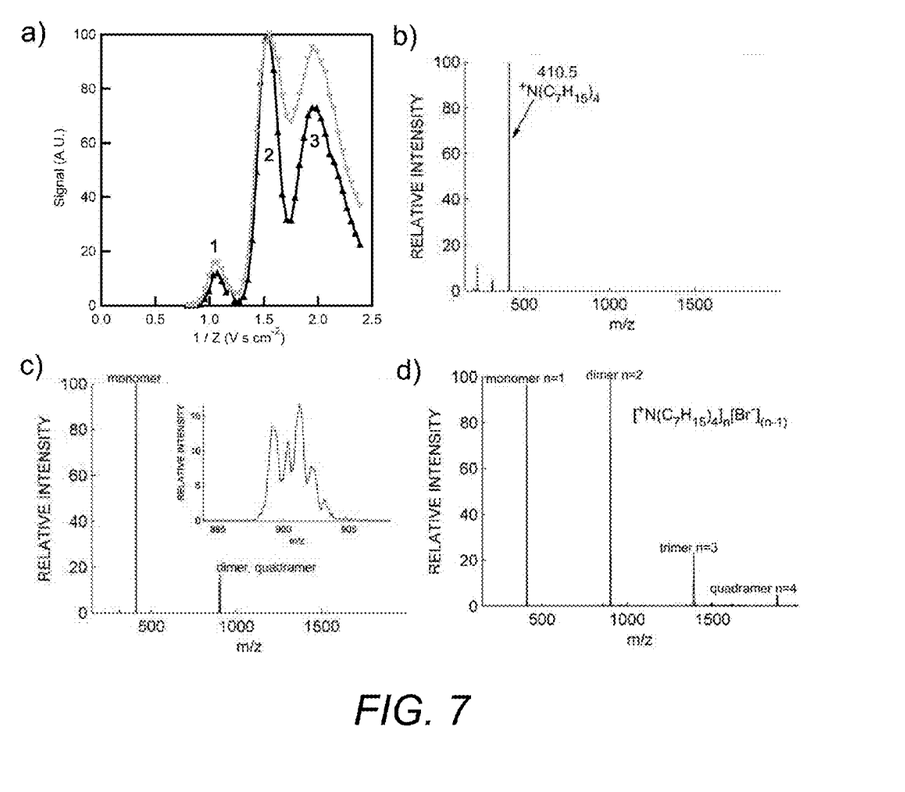
FIGS. 7(a)-7(d) illustrate mobility distritbutions of tetraheptylammonium for an extended compensation voltage scan and corresponding mass spectra in accordance with one or more embodiments of the invention.

An extended voltage scan was captured to confirm the identity of the suspected dimer and trimer peak for tetraheptylammonium bromide, as shown in FIG. 7. Thus, FIG. 7 illustrates mobility distributions of tetraheptylammonium for an extended compensation voltage scan and corresponding mass spectra. FIG. 7a illustrates inverse mobility spectrum for extended compensation voltage scan where three peaks are observed.

FIG. 7b illustrates mass spectrum acquired during elution of peak 1 where tetraheptylammonium monomer is observed. Accordingly, the mass spectrum for peak 1 consisted of a single mass at 410 m/z, which is the molecular weight of the tetraheptylammonium cation.

FIG. 7c illustrates mass spectrum acquired during elution of peak 2 where monomer and dimmer of tetraheptylammonium is observed. The region corresponding to the peak 2 consisted of three different species as detected in the mass spectrometer: singly charged monomer, singly charged dimer, and doubly charged quadramer. The observation of monomer may possibly be due to the transmission of the dimer (e.g., through the DMA) and subsequent fragmentation, into a monomer subunit, after analysis by the differential mobility instrument but before analysis with the LCQ-MS. The doubly charged quadramer is expected to have the same mobility as the singly charged dimmer, and this may explain its presence in the observed spectrum.

FIG. 7d illustrates mass spectrum acquired during elution of peak 3. Various multimers of tetraheptylammonium are observed. Thus, peak 3 in the distribution consisted of more molecular weights than the first, including the monomer, dimer, trimer, and quadramer, indicating that this peak is not due to a monomobile species. Mass analysis of the third peak in the extended mobility spectrum confirmed previous suspicions that the third peak in the mobility distribution was not due to a single species. It is possible that this peak is due to a multiply charged complex of several of the molecular ions which subsequently fragments during its transit between the nano-RDMA analyzer but before analysis with the mass spectrometer. Another possibility is that this peak is due to transmission of droplets of a particular size and charge (defining a mobility within range of operation of the nano-RDMA) which are then subsequently desolvated and the ions contained in it are analyzed in the mass spectrometer.

Smith and co-workers [2] have determined that in an electrospray, a distribution of droplet sizes and charges are present and while there are peak values for droplet size (determined by electrospray emitter size) and charge (likely determined by electrospray voltage and electric field between the electrospray needle and inlet capillary) there will, to some degree, be a class of droplets with some size and charge value such that this droplet will elute at a mobility value available to the nano-RDMA instrument. Although droplets may be very large, they can carry many more elementary charges than a simple ion and thus may have mobilities in ranges similar to ions.

Mobility distributions for Biomolecules: Gramicidin S

The exemplary nano-RDMA instrument described above may also be used for the analysis of biomolecules. Ion mobility-mass spectrometry has previously been applied to the analysis of cyclic peptides [3], and the cyclic decapeptide Gramicidin S was chosen for study with the nano-RDMA-ITMS instrument.

Figure 8:
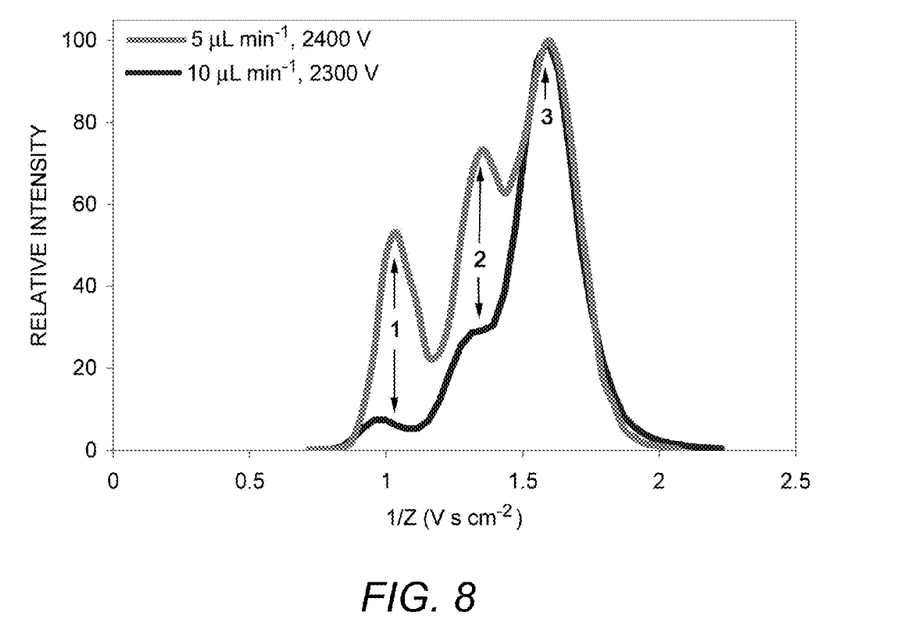
FIG. 8 is a mobility spectrum for two different electrospray conditions for decapeptide Gramicidin S in accordance with one or more embodiments of the invention.

FIG. 8 is a mobility spectrum for two different electrospray conditions for decapeptide Gramicidin S having the sequence cyclo-(VOL(dF)P)2, where O is the non-naturally occurring amino acid ornithine, and dF is d-phenylalanine. Gramicidin S was chosen as a system of study owing to the stability of the peptide, and the fact that it typically displays two charge states in a typical ESI spectrum having either one or both ornithine residues protonated.

Three peaks eluted from the nano-RDMA instrument. Peak 1 corresponds to the doubly charged monomer, while peak 2 corresponds to the singly charged monomer of Gramicidin S. Mass spectra recorded during peak 3 again shows the singly charged monomer of Gramicidin S, in higher abundance than previous. Thus, peak 3 also contains singly charged monomer, but judging by intensity and ability to drastically modulate height with electrospray conditions, it is suspected to be due to elution of droplets from the miniaturized ESI source. Higher liquid flow rate and lower spray voltage appears to promote formation of droplets relative to ions. Accordingly, the height of this peak could be modulated in different experiments by changing the characteristics of the ESI source, by either changing the spray voltage or changing the liquid flow rate. Since the detection of this peak appears to depend on the characteristics of the spray source, it is thought that this peak, like the third peak in the alkylammonium spectrum, may be due to the transmission of solvent droplets containing the peptide that are of the appropriate mobility, and are subsequently desolvated while travelling through the desolvation capillary of the mass spectrometer. Such "ghost peaks" likely due to solvent droplets have been observed in a previous account in the literature [4] but the composition of those peaks was not assigned.

Operation of Instrument as a General Front End for Mass Spectrometers

Embodiments of the invention provide an instrument that appears well suited to study a variety of systems from inorganic ions to biomolecules. Overall, the instrument resolution could be calculated from the mobility spectra to be a value of 7 for the tetraheptylammonium monomer. This is similar but slightly lower than what was observed when detecting the ions with a Faraday cup electrometer. The resolution could be readily changed through adjusting the aerosol flow. Although the resolution achieved in these experiments is less than that typically achieved in commercial instrumentation, it was nonetheless sufficient for separation of charge states in Gramicidin S. There are several techniques in the literature to "charge strip" a species so that a lower charge state can be obtained before subsequent reaction or mass analysis. The instrument of embodiments of the invention could pre-separate charge states before analysis without the use of such chemical charge stripping methods.

No special considerations for differential pumping may be necessary when interfacing a DMA and ITMS instruments. Normally, the transfer of ions from atmospheric pressure into vacuum for mass analysis requires a differential pumping scheme, where a series of skimmer lenses and orifices mediate the transition between high and low pressure. However, in embodiments of the invention, the interfacing between the DMA instrument (e.g., a nano-RDMA instrument) and the ITMS takes place at atmospheric pressure, greatly simplifying the interface and requirements for it. The fact that the outlet of the DMA can be placed directly in front of the inlet of the mass spectrometer with a minimum of effort suggests that this technique of interfacing the DMA instrument to atmospheric pressure inlet mass spectrometers is nearly universal, provided the mass spectrometer in question has sufficient duty cycle and sensitivity.

It appears, then, that a DMA-MS system can be somewhat universal in that one may place a DMA instrument as a front end to any atmospheric pressure inlet mass spectrometer, and is not limited to use with particular MS (e.g., Thermo™ LCQ instruments). Other instruments to which this interface may be well suited include Thermo LTQ™, Thermo LTQ Orbitrap™, Thermo LTQ-FT™, and many of the Agilent™ ion trap mass spectrometers. In addition, the DMA may also interface with time of flight instruments such as Waters QTof™ or others.

Conclusion

This concludes the description of the preferred embodiment of the invention. The following describes some alternative embodiments for accomplishing the present invention.

A DMA-MS system (e.g., a nano-RDMA-ITMS system) may be utilized to achieve mobility-MS analysis of organic molecules and small peptides. An exemplary particular system is the interfacing of an existing nano-RDMA instrument to a laboratory mass spectrometer in a simple and effective manner. When interfacing the nano-RDMA instrument to another instrument with an atmospheric pressure inlet, no special differential pumping considerations are required and it appears that the nano-RDMA-MS interface is applicable to a variety of mass spectrometer systems.

It may be noted that RDMAs may be preferable to other shaped DMAs. For example, while other DMA shapes exist (see [6][9]), prior art DMA devices may operate in extreme conditions. For example, such prior art DMA devices may require high Reynold's numbers (e.g., over 2000) for proper operation. Such high Reynold's numbers may require a high gas flow rates. For example, a gas flow rate of 1-5 liters per minute (LPM) may be used to produce a sheath flow rate of 59-825 LPM. Such high gas flow rates increase the operating costs (e.g., by requiring larger volumes of purified gas and components capable of processing the high gas flow rates) and are improbable for many laboratories and commercial production.

In contrast to prior art DMA based devices, embodiments of the present invention may utilize a nano-RDMA for separating the ionized sample by mobility. Nano-RDMA devices are smaller than those required by prior art large flow devices. Accordingly, the size of such nano-RDMA devices may enable field deployment and does not require large volumes of purified gas (gas processed by the mobility separator should produce a gas that is free of contaminants that can be detected by the mass spectrometer performing the mass analysis. Thus, a nano-RDMA device may typically have lower gas flow rates as well as lower Reynolds numbers. For example, embodiments of the invention may have Reynolds numbers of approximately 200 and a gas flow rate of 1-2 liters per minute. Such a gas flow rate may result in a sheath flow rate of 5-50 liters per minute (max) (with a more preferable rate of either 10 liters per minute or 20 liters per minute).

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

Logical Flow

Figure 9:
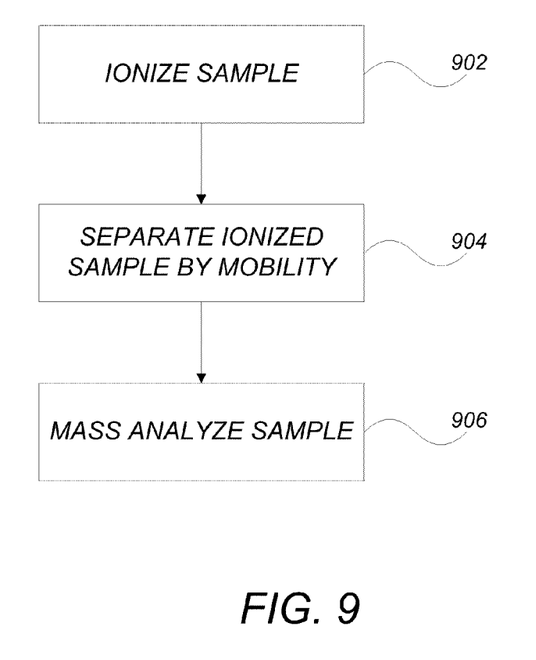
FIG. 9 illustrates the logical flow for analyzing a sample in accordance with one or more embodiments of the invention.

FIG. 9 illustrates the logical flow for analyzing a sample in accordance with one or more embodiments of the invention.

At step 902, a sample is ionized using a first ionization system. The first ionization system may be an electrospray source such as an electrospray ionization emitter (ESI). Alternatively, the ionization system may be an atmospheric pressure chemical ionization system.

At step 904, the ionized sample is separated by mobility using a nano-radial differential mobility analyzer (nano-RDMA)(i.e., a nano-sized RDMA). Alternatively, other shaped DMAs may be utilized (e.g., shapes other than radial) while remaining nano-size. Similarly, larger (non-nano sized) DMAs may be utilized that are radially shaped in accordance with embodiments of the invention.

The nano-RDMA is coupled to the first ionization system (e.g., using standard Swagelok™ fittings). The nano-RDMA is also coupled to a mass spectrometer (e.g., using a breadboard plate made for mounting optical elements, a pair of mounting plates, and optic mounting posts). In addition, the sample outlet of the nano-RDMA is aligned with an atmospheric pressure inlet (API) of the mass spectrometer. A gap between the sample outlet and the API may be minimized by empirically adjusting a position of the nano-RDMA. A sheath flow rate of/produced by the nano-RDMA may be a maximum of fifty (50) liters per minute. In this regard, the sheath flow rate provided by the nano-RDMA is lower as compared to a sheath flow rate produced by a continuous flow mobility classifier-mass spectrometer system without the nano-RDMA.

At step 906, the separated sample is mass analyzed using the mass spectrometer. The mass spectrometer may be a liquid chromatography-mass spectrometer (LC-MS or LCQ-MS).

REFERENCES

The following publications/patents/patent applications are incorporated by reference herein.

[1] Brunelli, N. A.; Flagan, R. C.; Giapis, K. P. *Aerosol Sci. Tech.* 2009, 43, 53-59.

[2] Smith, J. N.; Flagan, R. C.; Beauchamp, J. L. *J. Phys. Chem. A* 2002, 106, 9957-9967.

[3] Ruotolo, B. T.; Tate, C.C.; Russel, D. H. *J. Am. Soc. Mass Spectrom.* 2004, 15, 870-878.

[4] Guevremont, R.; Siu, K. W. M.; Wang, J.; Ding, L. *Anal. Chem.* 1997, 69, 3959-3965.

[5] Ude, S.; de la Mora, J. F. *J. Aerosol Sci.* 2005, 36, 1224-1237.

[6] Flagan, On Differential mobility analyzer resolution, *Aerosol Science and Technology* (1999) vol. 30 (6), pp. 556-570.

[7] U.S. Pat. No. 5,117,190 issued on May 26, 1992 to Michel Pourprix.

[8] U.S. Pat. No. 5,596,136 issued on Jan. 21, 1997 to Richard C. Flagan and Shou-Hua Zhang.

[9] Jingkun Jian, Michel Attoui, Michael Heim, Nicholas A. Brunelli, Peter H. McMurry, Gerhard Kasper, Richard C. Flagan, Konstantinos Giapis, and Guillaume Mouret, Transfer Functions and Penetrations of Five Differential Mobility Analyzers for Sub-2 nm Particle Classification, *Aerosol Science and Technology* (Jan. 15, 2011) 45:4, 480-492.

[10] U.S. Pat. No. 5,869,831 issued on Feb. 9, 1999 to Juan Fernandez De La Mora, Luis De Juan, Thilo Eichler, and Joan Rosell.

[11] United States Patent Application Publication No. 2008/0251714 filed on Apr. 11, 2007 by Rus-Perez Juan and Juan Fernandez de la Mora.

[12] L. de Juan and J. Fernandez de la Mora, High Resolution Size Analysis of Nanoparticles and Ions: Running a Vienna DMA of Near Optimal Length at Reynolds Numbers up to 5000, *Journal of Aerosol Science*, (1998), vol. 29, No. 5/6, pp. 617-626.

What is claimed is:

1. A continuous flow mobility classifier-mass spectrometer system comprising:
    (a) a first ionization system configured to ionize analyte molecules in a sample;
    (b) a continuous flow radial differential mobility analyzer (RDMA) configured to analyze the ionized analyte molecules in a first dimension, wherein:
        (i) the RDMA is coupled to the first ionization system;

(ii) the RDMA is coupled to a mass spectrometer;
(iii) the sample is introduced into the RDMA;
(iv) the RDMA is configured to employ axial electric fields to separate the ionized analyte molecules by mobility; and
(c) the mass spectrometer configured to analyze the ionized analyte molecules in a second dimension, wherein:
(i) a continuous flow of the ionized analyte molecules that have been separated by mobility are introduced to the mass spectrometer to determine a mass-to-charge ratio of a charged particle within the mobility separated ionized analyte molecules; and
wherein:
a sheath flow rate provided by the RDMA is lower as compared to a sheath flow rate produced by a continuous flow mobility classifier-mass spectrometer system without the RDMA;
an instrument resolution of the RDMA has a value of at least seven (7);
a sample outlet of the RDMA is aligned with an atmospheric pressure inlet (API) of the mass spectrometer; and
a gap between the sample outlet and the API is minimized by adjusting a position of the RDMA.

2. The continuous flow mobility classifier-mass spectrometer of claim 1, wherein the ionization system comprises an electrospray source.

3. The continuous flow mobility classifier-mass spectrometer of claim 2, wherein the electrospray source comprises an electrospray ionization emitter (ESI).

4. The continuous flow mobility classifier-mass spectrometer of claim 1, wherein the ionization system comprises an atmospheric pressure chemical ionization system.

5. The continuous flow mobility classifier-mass spectrometer of claim 1, wherein a second ionization system was removed from the mass spectrometer prior to coupling the mass spectrometer to the RDMA.

6. The continuous flow mobility classifier-mass spectrometer of claim 1, wherein the mass spectrometer comprises a liquid chromatography-mass spectrometer (LC-MS).

7. The continuous flow mobility classifier-mass spectrometer of claim 1, wherein the first ionization system is coupled to the RDMA using standard Swagelok™ fittings.

8. The continuous flow mobility classifier-mass spectrometer of claim 1, wherein a sheath flow rate of the RDMA is a maximum of fifty (50) liters per minute.

9. A method for analyzing a sample comprising:
(a) ionizing analyte molecules in a sample using a first ionization system;
(b) analyzing the ionized analyte molecules in a first dimension by separating the ionized analyte molecules by mobility using a continuous flow radial differential mobility analyzer (RDMA) that employs axial electric fields, wherein:
(i) the RDMA is coupled to the first ionization system;
(ii) the RDMA is coupled to a mass spectrometer; and
(iii) the sample is introduced into the RDMA;
(c) introducing a continuous flow of the ionized analyte molecules that have been separated by mobility to the mass spectrometer;
(d) analyzing the ionized analyte molecules in a second dimension by mass analyzing the ionized analyte molecules that have been separated by mobility using the mass spectrometer to determine a mass-to-charge ratio of a charged particle within the mobility separated ionized analyte molecules; and
wherein:
a sheath flow rate provided by the RDMA is lower as compared to a sheath flow rate produced by a continuous flow mobility classifier-mass spectrometer system without the RDMA;
an instrument resolution of the RDMA has a value of at least seven (7);
a sample outlet of the RDMA is aligned with an atmospheric pressure inlet (API) of the mass spectrometer; and
a gap between the sample outlet and the API is minimized by adjusting a position of the RDMA.

10. The method of claim 9, wherein the ionization system comprises an electrospray source.

11. The method of claim 10, wherein the electrospray source comprises an electrospray ionization emitter (ESI).

12. The method of claim 9, wherein the ionization system comprises an atmospheric pressure chemical ionization system.

13. The method of claim 9, wherein the mass spectrometer comprises a liquid chromatography-mass spectrometer (LC-MS).

14. The method of claim 9, wherein a sheath flow rate of the RDMA is a maximum of fifty (50) liters per minute.

* * * * *